United States Patent [19]

Karami

[11] 4,005,712
[45] Feb. 1, 1977

[54] DISPOSABLE DIAPER WITH ADJUSTABLE TAPE FASTENER

[75] Inventor: Hamzeh Karami, Crystal Lake, Ill.

[73] Assignee: Colgate-Palmolive Company, New York, N.Y.

[22] Filed: Nov. 3, 1975

[21] Appl. No.: 628,438

[52] U.S. Cl. .............................. 128/284; 128/287; 128/290 R

[51] Int. Cl.² .......................................... A61F 13/16

[58] Field of Search ...... 128/284, 285, 287, 290 R, 128/290 H, 296, 298

[56] References Cited

UNITED STATES PATENTS

| | | | |
|---|---|---|---|
| 3,750,669 | 8/1973 | De Luca | 128/287 |
| 3,926,191 | 12/1975 | Trisch | 128/284 |
| 3,926,191 | 12/1975 | Tritsch | 128/287 |
| 3,927,674 | 12/1976 | Schaar | 128/284 |
| 3,930,501 | 1/1976 | Schaar | 128/287 |
| 3,948,268 | 4/1976 | Karami | 128/287 |

*Primary Examiner*—Russell R. Kinsey
*Assistant Examiner*—Robert F. Cutting
*Attorney, Agent, or Firm*—Powell L. Sprunger

[57] ABSTRACT

A disposable diaper comprising, an absorbent pad assembly having opposed surfaces, and a side edge. The diaper has a tape fastener comprising, an elongated pressure-sensitive tape strip having an adhesive surface, a first end portion secured to one of the surfaces of the pad assembly adjacent the side edge, and a second attachment end portion extending past the side edge. The fastener has an adjustment member comprising an elongated sheet having a first section fixedly attached to the diaper, and a second section releasably attached to an adhesive area on the second strip portion. The second sheet section is spaced from an end of the second strip portion to expose a region of adhesive for use in securing the diaper about an infant, and the second sheet section is peelable from the strip to selectively enlarge the region of adhesive.

11 Claims, 7 Drawing Figures

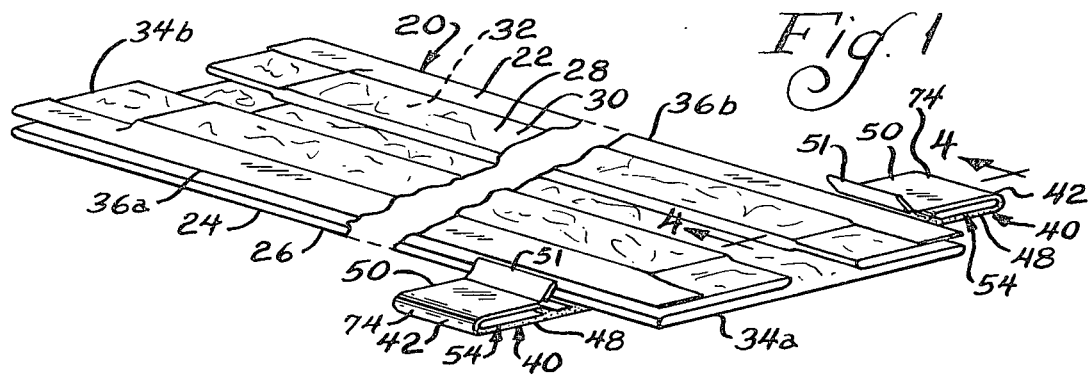

DISPOSABLE DIAPER WITH ADJUSTABLE TAPE FASTENER

BACKGROUND OF THE INVENTION

The present invention relates to absorbent articles, and more particularly to disposable diapers.

In recent years diapers of the disposable type have come into widespread use. For convenience, such disposable diapers have often been provided with tape fasteners to eliminate necessity for separate attachment devices, such as pins. The tape fasteners may comprise tape strips and release sheets to cover adhesive on the strips. During placement of the diaper, the tape strips are peeled from the release sheets after which the strips are utilized to secure the diaper about an infant.

Although such tape fasteners have been found desirable for use on disposable diapers, certain problems remain with the fasteners. In particular, the fasteners have not been adaptable to accommodate the varying size of infants about which the diapers may be placed. For older infants having a relatively large waist size, the tape strips may have a relatively small adhesive region for use in securing the diaper about the infant. However, if such tape strips are utilized on a younger baby having a relatively small waist size, the strips will cause the diaper to gap away from the smaller infant. Accordingly, an adhesive area of increased size should be utilized on the tape strips for smaller infants.

SUMMARY OF THE INVENTION

A principal feature of the present invention is the provision of a tape fastener for a disposable diaper which is adjustable for use on infants having varying waist sizes.

The diaper of the present invention comprises, an absorbent pad assembly having opposed surfaces, and a side edge. The diaper also has a tape fastener comprising, an elongated pressure-sensitive tape strip having an adhesive surface, first and third spaced adhesive zones located adjacent opposed ends of the strip, and a second adhesive zone intermediate the first and third zones. The first zone is attached to one of the surfaces of the pad assembly adjacent the side edge, and the second and third zones extend past the side edge. The tape fastener also has an adjustment member comprising an elongated sheet having a first surface with a relatively low affinity for adhesive on the strip, a second opposed surface with a relatively high affinity for adhesive on the strip, and a pair of end edges. The sheet has a first end section defined by one of the end edges and a fold line in the sheet, with the first sheet section being releasably attached to adhesive in the second zone, with the first surface of the first sheet section facing adhesive in the second zone, with the fold line being located adjacent the juncture of the second and third adhesive zones, and with the one end edge of the sheet being spaced from the side edge of the pad assembly. The sheet has a second section which is folded back along the fold line with the second surface of the second sheet section facing the second surface of the first sheet section. The sheet has a third end section extending between the second sheet section and the other of the end edges, with the third section being fixedly attached to adhesive on the second zone intermediate the one end edge of the first sheet section and the side edge of the pad assembly, and with the second surface of the third sheet section facing adhesive on the strip. The third adhesive zone of the strip is releasably attached to the first surface of the second sheet section.

Thus, a feature of the present invention is that the tape strip may be peeled from the first surface of the second sheet section to expose the third adhesive zone and provide a region of adhesive for securing the diaper about an infant having a first waist size.

Another feature of the present invention is that the first sheet section may be peeled from the second adhesive zone to enlarge the adhesive securing region and secure the diaper about an infant having a second reduced waist size.

Accordingly, a feature of the present invention is that the tape fastener may be utilized to snugly secure the diaper about infants having varying waist sizes.

Yet another feature of the invention is that the third sheet section retains the sheet on the tape strip and eliminates the necessity for separately discarding the sheet.

Further features will become more fully apparent in the following description of the embodiments of this invention and from the appended claims.

DESCRIPTION OF THE DRAWINGS

In the drawings:

FIG. 1 is a fragmentary perspective view of a disposable diaper having a tape fastener according to the present invention;

FIG. 2 is a fragmentary front plan view of the diaper of FIG. 1 showing the tape fastener in position for securing the diaper about an infant having a relatively large waist size;

FIG. 3 is a fragmentary sectional view taken substantially as indicated along the line 3—3 of FIG. 2;

FIG. 4 is a fragmentary sectional view taken substantially as indicated along the line 4—4 of FIG. 1;

FIG. 5 is a fragmentary sectional view illustrating a sheet in the tape fastener being peeled from a tape strip to enlarge a securing adhesive region and attach the diaper about an infant having a relatively small waist size;

FIG. 6 is a fragmentary sectional view showing the sheet of FIG. 5 as removed to a remote position relative the tape strip; and FIG. 7 is a fragmentary sectional view of another embodiment of the present invention.

DESCRIPTION OF THE PREFERRED EMBODIMENTS

Referring now to FIG. 1, there is shown a disposable diaper 20 having an absorbent pad assembly 22. The pad assembly 22 has a fluid impervious backing sheet 24 defining a back surface 26 of the pad assembly, a fluid pervious top sheet 28 defining an opposed front surface 30 of the pad assembly, and an absorbent pad 32 intermediate the backing sheet 24 and top sheet 28. The pad assembly 22 has a pair of end edges 34a and 34b, and a pair of side edges 36a and 36b connecting the end edges 34a and b. The pad assembly 22 may be folded along a plurality of longitudinally extending fold lines to define a box-pleat configuration, as shown.

The diaper 20 also has a pair of tape fasteners generally designated 40 for securing the diaper about an infant. As shown in FIGS. 2 and 3, the tape fasteners 40 have an elongated pressure-sensitive tape strip 42 having an adhesive 44. The tape strip 42 has first and third spaced adhesive zones 46 and 50, respectively, adjacent opposed inner and outer ends 47 and 51, respectively, of the tape strip 42. The tape strip 42 also has a second adhesive zone 48 intermediate the first and third zones 46 and 50. As shown, the first adhesive zone 46 of the tape strip 42 is fixedly attached to the back surface 26 of the pad assembly 22, with the second and third adhesive zones 48 and 50 extending past the side edge 36b of the pad assembly.

The tape fastener 40 has an adjustment member generally designated 54 comprising an elongated sheet 56 of a suitable material, such as paper, having a first surface 58 which has a relatively low affinity for adhesive on the strip 42 and a second opposed surface 60 which has a relatively high affinity for adhesive on the strip 42. The sheet surfaces 58 and 60 may be suitably treated to provide the desired affinities for adhesive 44 on the tape strips 42. For example, a paper sheet may have its first surface 58 treated with silicone to provide a release surface for the sheet.

As shown, the sheet 56 has a first end section 62 extending between a first end edge 64 of the sheet 56 and a fold line 66 in the sheet 56. The first sheet section 62 is releasably attached to the second adhesive zone 48 with the first release surface 58 of the first section 62 facing the adhesive 44 in the second strip zone 48. The sheet fold line 66 is located adjacent the juncture of the second and third adhesive zones 48 and 50, respectively, and the first end edge 64 of the sheet 56 is spaced from the side edge 36b of the pad assembly 22. The sheet 56 has a second section 68 which is folded along the fold line 66 of the sheet 56, such that the second surface 60 of the second section 68 faces the second surface 60 of the first end section 62.

The sheet 56 also has a third end section 70 which extends between the second sheet section 68 and a second end edge 72 of the sheet 56. As shown, the third sheet section 70 also extends past the first end edge 64 of the first sheet section 62. The second surface 60 of the third end section 70 faces the adhesive 44 in the second adhesive zone 48 at a location intermediate the first end edge 64 of the sheet 56 and the side edge 36b of the pad assembly 22, such that the third end section 70 of the sheet 56 is fixedly attached to the tape strip 42.

As shown in FIGS. 1 and 4, the outer end 51 of the tape strip 42 is folded over the sheet 56 along a fold line 74, such that the third adhesive zone 50 is releasably attached to the first release surface 58 of the second sheet section 68. Accordingly, the outer end 51 of the tape strip 42 is releasably retained on the sheet 56 of the adjustment member 54 until the diaper is ready for use. Also, the outer end of the tape assembly, comprising the second and third zones of the tape strip and the adjustment member, may be folded over and secured to the front or back surfaces of the diaper to facilitate packaging of the diaper, if desired.

When it is desired to place the diaper 20 about an infant, the outer end 51 of the tape strip 42 may be peeled from the first surface 58 of the sheet 56 to expose the third adhesive zone 50, as shown in FIGS. 2 and 3. The tape fasteners 40 may be utilized in this configuration to secure the diaper 20 about an infant having a relatively large waist size, with only the third adhesive zones 50 on the tape strips 42 being used to secure the diaper about such an infant. However, if the tape fasteners are utilized in this configuration on an infant having a relatively small waist size, the tape strips would permit the diaper to gap away from the smaller infant.

Accordingly, the first sheet section 62 of the adjustment member 54 may be peeled away from adhesive in the second adhesive zone 48, as shown in FIG. 5, to enlarge the securing adhesive region of the tape strips 42 for placement of the diaper about an infant having a relatively small waist size. The first sheet section 62 may be unfolded from the second sheet section 68, as shown in FIG. 6, and the first sheet section 62 may be placed above the front surface 30 of the pad assembly 22 to remove the sheet from the enlarged adhesive region. Thus, the enlarged adhesive region comprises the third adhesive zone 50 and the outer portion of the second adhesive zone 48. As shown in FIG. 6, the third sheet section 70 permanently retains the sheet 56 to the tape strip, and eliminates the necessity of separately discarding the sheet during placement of the diaper. In this configuration, the tape fasteners 40 may be utilized to secure the diaper 20 about an infant having a relatively small waist size without the diaper gapping away from the infant after the diaper has been placed.

It will be apparent that the length of the first sheet sections 62 may be suitably selected to expose an enlarged adhesive region of desired size. In the embodiment shown, the third end sections 70 of the sheets 56 are located adjacent the side edges 36a and b of the pad assembly 22, and the first end edges 64 of the sheets 56 are located adjacent the third end sections 70. As shown in FIG. 7, the third end sections 70 of the sheets 56 may include an extension 80 which is positioned over and secured to the front surface 30 of the pad assembly by suitable means, such as adhesive 82. The extensions 80 serve to anchor the tape strip to the front of the diaper, as well as the back, and thus reinforce the tape fastener.

The foregoing detailed description is given for clearness of understanding only, and no necessary limitations should be understood therefrom, as modifications will be obvious to those skilled in the art.

I claim:

1. A disposable diaper, comprising:
   an absorbent pad assembly having opposed surfaces, and a side edge; and
   a tape fastener comprising,
      an elongated pressure-sensitive tape strip having an adhesive surface, a first end portion secured to one of said surfaces of the pad assembly adjacent said side edge, and a second attachment end portion extending past said side edge, and
      an adjustment member comprising an elongated sheet having first and second surfaces and a pair of end edges, said sheet having a first end section intermediate one of said end edges and a fold line in the sheet, said first section being attached to the second end portion of said tape strip with the first surface of said first section facing adhesive on said strip, said sheet having a second intermediate section folded back along said fold line with the second surface of the second section facing the second surface of the first section, and said sheet having a third section extending from the second section and extending past said one end edge of the first section, said third section section being attached to said strip with the second surface of the third section facing adhesive on said strip, said fold line being spaced from an end of said second end portion of the tape strip to expose a region of adhesive for use in securing the diaper about an infant, the first surface of said first sheet section having a relatively low affinity for adhesive, whereby said first section may be peeled from said tape strip to enlarge said adhesive securing region, and the second surface of said third sheet section having a relatively high affinity for adhesive, whereby said third section retains said sheet to the tape strip.

2. The diaper of claim 1 wherein all of said first sheet surface has a relatively low affinity for adhesive on said strip.

3. The diaper of claim 1 wherein said fold line is spaced from an outer end of said second strip portion.

4. The diaper of claim 3 wherein said third sheet section is attached to the strip adjacent said side edge of the pad assembly.

5. The diaper of claim 3 wherein the first surface of said second sheet section has a relatively low affinity for adhesive, and in which an outer end portion of said strip is releasably attached to the first surface of said second sheet section.

6. The diaper of claim 3 wherein said third section includes an extension secured to the other of said opposed surfaces of the pad assembly.

7. The diaper of claim 1 wherein all of said second sheet surface has a relatively high affinity for adhesive on said strip.

8. The diaper of claim 1 wherein said one end edge of the first sheet section is located adjacent said third sheet section.

9. A disposable diaper comprising:
an absorbent pad assembly having opposed surfaces, and a side edge; and
a tape fastener comprising,
an elongated pressure-sensitive tape strip having an adhesive surface, a first end portion secured to one of said surfaces of the pad assembly adjacent said side edge, and a second attachment end portion extending past said side edge, and
and adjustment member comprising an elongated sheet having a first section fixedly attached to said diaper, and a second section releasably attached to an adhesive area on said second strip portion, with said second sheet section being spaced from an end of said second strip portion to expose a region of adhesive for use in securing the diaper about an infant, and with said second sheet section being peelable from said strip to selectively enlarge said region of adhesive.

10. The diaper of claim 9 wherein said sheet includes a release surface facing away from adhesive on said strip, and in which a part of said second strip portion is releasably attached to said release surface.

11. A disposable diaper, comprising:
an absorbent pad assembly having opposed surfaces, and a side edge; and
a tape fastener comprising,
an elongated pressure-sensitive tape strip having an adhesive surface, first and third spaced adhesive zones located adjacent opposed ends of the strip, and a second adhesive zone intermediate said first and third zones, with said first zone being attached to one of said surfaces of the pad assembly adjacent said side edge, and with said second and third zones extending past said side edge, and
an adjustment member comprising an elongated sheet having a first surface with a relatively low affinity for adhesive on said strip, a second opposed surface with a relatively high affinity for adhesive on said strip, a pair of end edges, a first end section defined by one of said end edges and a fold line in said sheet, said first sheet section being releasably attached to adhesive in said second zone with the first surface of said first sheet section facing adhesive in said second zone, with said fold line being located adjacent the juncture of said second and third adhesive zones, and with said one end edge being spaced from said side edge of the pad assembly, said sheet having a second section being folded back along said fold line with the second surface of the second sheet section facing the second surface of the first sheet section, said sheet having a third end section extending between said section sheet section and the other of said end edges, said third sheet section being fixedly attached to adhesive on said second zone intermediate said one end edge of said first sheet section and said side edge of the pad assembly with the second surface of the third sheet section facing adhesive on said strip, and said third adhesive zone of said tape strip being releasably attached to the first surface of said second sheet section, whereby said tape strip may be peeled from the first surface of said second sheet section to expose said third adhesive zone and provide a region of adhesive for securing the diaper about an infant, and said first sheet section may be peeled from said second adhesive zone to enlarge said adhesive securing region while said third sheet section retains the sheet to the tape strip.

* * * * *